United States Patent
Hansson

(10) Patent No.: US 7,029,476 B2
(45) Date of Patent: Apr. 18, 2006

(54) DEVICE AT FIXING MEANS FOR FIXATION OF BONE FRAGMENTS AT BONE FRACTURES

(76) Inventor: Henrik Hansson, Eriksberg, Vreta Kloster (SE) S-590 77

(*) Notice: Subject to any disclaimer, the term of this patent is extended or adjusted under 35 U.S.C. 154(b) by 0 days.

(21) Appl. No.: 10/343,403

(22) PCT Filed: Jul. 31, 2001

(86) PCT No.: PCT/SE01/01684

§ 371 (c)(1),
(2), (4) Date: Jan. 29, 2003

(87) PCT Pub. No.: WO02/11632

PCT Pub. Date: Feb. 14, 2002

(65) Prior Publication Data
US 2004/0073220 A1    Apr. 15, 2004

(30) Foreign Application Priority Data
Aug. 9, 2000   (SE) ................................. 0002855

(51) Int. Cl.
A61B 17/56   (2006.01)
A61F 2/30    (2006.01)
(52) U.S. Cl. ...................................................... 606/72
(58) Field of Classification Search ............ 606/62, 606/64, 72, 75, 53, 60, 73, 86, 96, 97, 103, 606/104
See application file for complete search history.

(56) References Cited

U.S. PATENT DOCUMENTS

| | | | | |
|---|---|---|---|---|
| 2,267,925 A | * | 12/1941 | Johnston | 606/66 |
| 2,570,465 A | * | 10/1951 | Lundholm | 606/65 |
| 2,631,584 A | * | 3/1953 | Purificato | 606/68 |
| 2,998,007 A | * | 8/1961 | Herzog | 606/63 |
| 3,497,953 A | * | 3/1970 | Weissman | 433/173 |
| 4,498,468 A | | 2/1985 | Hansson | |
| 5,257,996 A | * | 11/1993 | McGuire | 606/104 |
| 5,810,820 A | * | 9/1998 | Santori et al. | 606/63 |
| 5,814,047 A | * | 9/1998 | Emilio et al. | 606/62 |
| 5,971,986 A | * | 10/1999 | Santori et al. | 606/62 |
| 6,074,392 A | | 6/2000 | Durham | |
| 6,200,321 B1 | * | 3/2001 | Orbay et al. | 606/96 |
| 6,273,892 B1 | * | 8/2001 | Orbay et al. | 606/96 |
| 6,558,388 B1 | * | 5/2003 | Bartsch et al. | 606/62 |

FOREIGN PATENT DOCUMENTS

| | | |
|---|---|---|
| EP | 0064724 A2 | 11/1982 |
| FR | 2668920 A1 | 5/1992 |
| WO | WO9531942 A1 | 11/1995 |
| WO | WO0211632 A1 | 2/2002 |

* cited by examiner

Primary Examiner—Eduardo C. Robert
Assistant Examiner—Anuradha Ramana
(74) Attorney, Agent, or Firm—Tarolli, Sundheim, Covell & Tummino L.L.P.

(57) ABSTRACT

The present invention relates to a device at fixing means for fixation of bone fragments at bone fractures, wherein the fixing means (1) preferably is a spike for thigh-bone necks for fixation of bone fragments (2.3) at fractures (4) of the thigh-bone neck. The fixing means (1) comprises a sleeve (5) and a pin (7) provided therein. The pin (7) includes a front part (7a) which is directed obliquely forward relative to a rear part (7e) thereof and towards front parts (9a) of a second wall surface (9) close to a guide surface (12) of the sleeve (5) when the pin (7) is located in a ready position (B) in said sleeve (5).

17 Claims, 3 Drawing Sheets

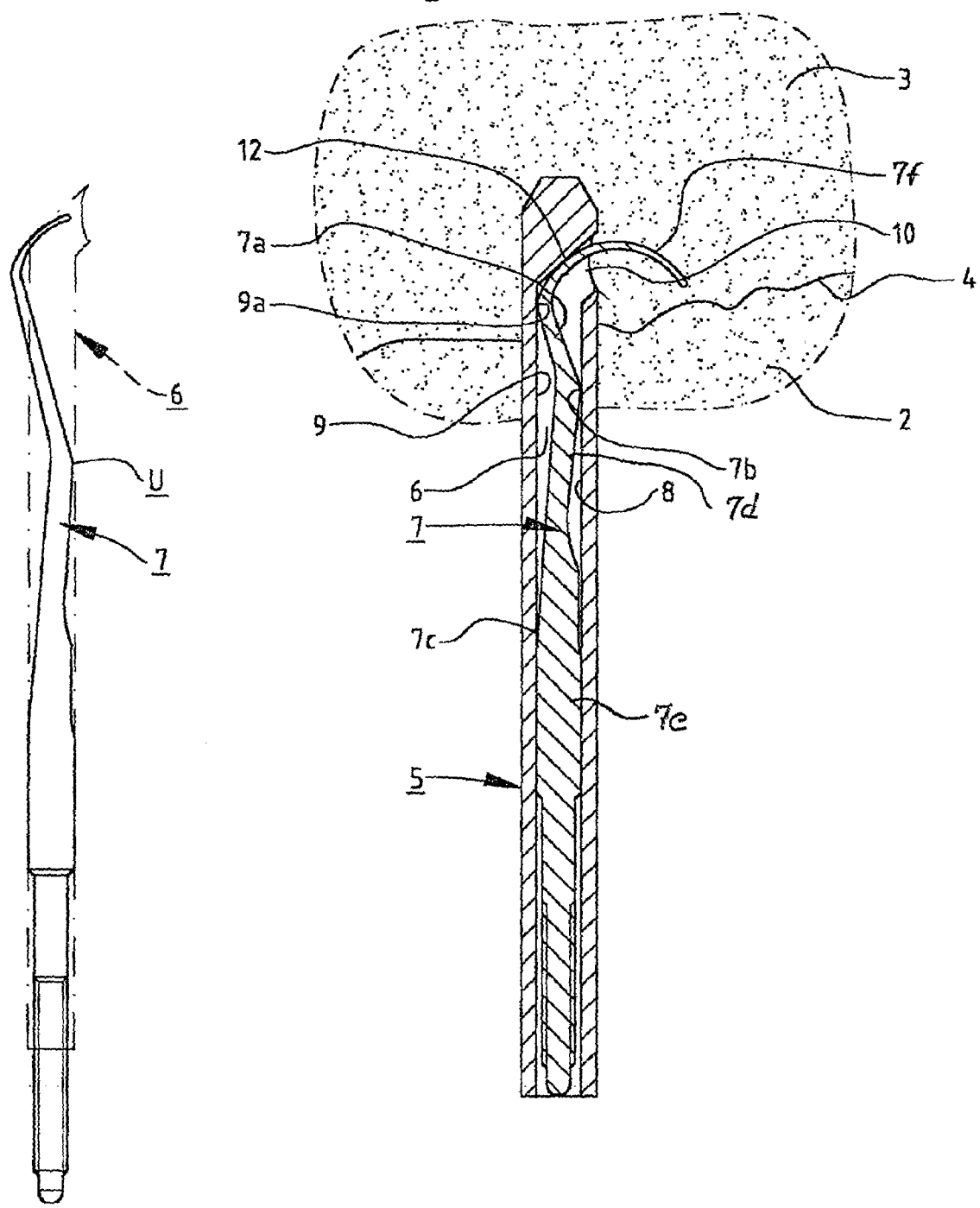

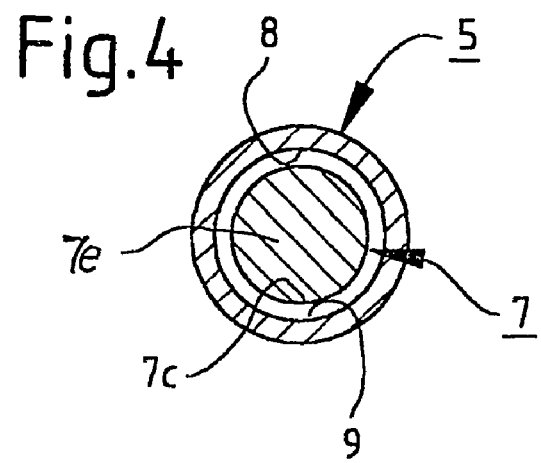
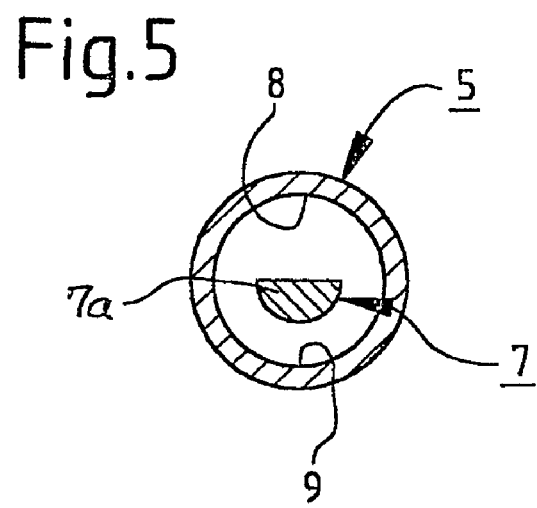
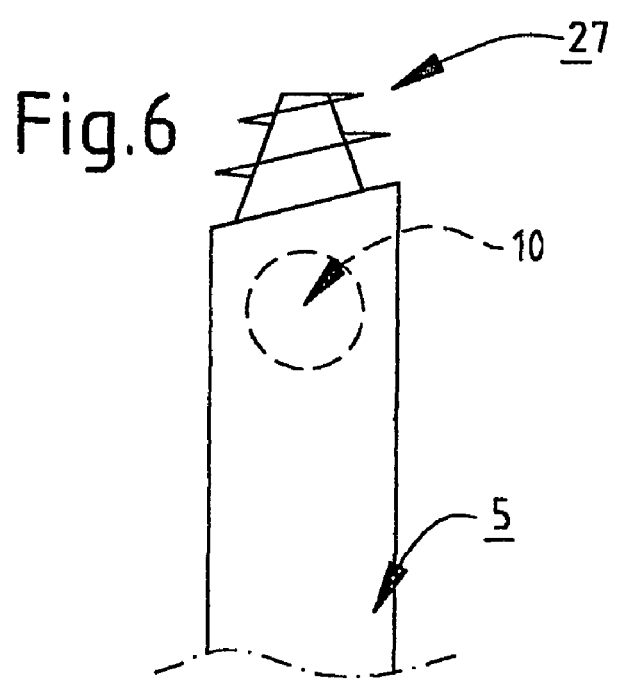

DEVICE AT FIXING MEANS FOR FIXATION OF BONE FRAGMENTS AT BONE FRACTURES

FIELD OF THE INVENTION

The present invention relates to a device at fixing means for fixation of bone fragments at bone fractures, wherein the fixing means preferably is a spike for thigh-bone necks for fixation of bone fragments at fractures of the thigh-bone neck, wherein the fixing means comprises a sleeve which is open at the rear for insertion of a pin into a ready position, wherein the sleeve defines an elongated space with two opposite wall surfaces, namely a first longitudinal wall surface in which there is provided a side opening and a longitudinal second wall surface from which a guide surface extends in an inclined forward direction to a front edge of the side opening, and wherein the guide surface is provided to guide a front, preferably curved end portion of the pin to force its way out through the side opening when said pin is displaced in a forward direction relative to the sleeve.

BACKGROUND OF THE INVENTION

Fixing means of the abovementioned type are known from SE 431 053 (U.S. Pat. No. 4,498,468) and have operated satisfactory for many years.

There is however, always a risk that the pin does not find its way out through the side opening, but is deformed inside the sleeve if it occupies or is brought to occupy an erroneous position in relation thereto. This may be due to that the pin unintentionally moves or is moved from a ready position, e.g. by being turned or rotated relative to the sleeve through the influence from rotatable members of a driving or actuator instrument. There is also a risk that those parts of the front end portion of the pin which are driven into surrounding bone material are not deformed into an advantageous curvature. This results in that there is a risk that the fixing means does not get the intended function, namely stable fixation of the bone fragments relative to each other. There is also a risk that the front end portion of the pin due to a faulty design penetrates the bone fragment it is forced into.

BRIEF SUMMARY OF THE INVENTION

The object of the present invention has been to eliminate this problem and this is arrived at by providing the abovementioned device with the characterizing features of subsequent claim 1.

By providing the device with said characterizing features, the pin is prevented from unintentional movement out of a ready position and/or is it ensured that the end portion of the pin gets an advantageous curvature such that a stable fixation of the bone fragment is obtained and the likelihood that said pin penetrates the bone fragment is reduced.

BRIEF DESCRIPTION OF THE DRAWINGS

The invention will be further described below with references to the accompanying drawings, in which:

FIG. 2 illustrates the fixing means of FIG. 1 with a front portion of a pin protruding from a sleeve;

FIG. 3 illustrates a pin forming part of the fixing means of FIG. 1, in an unstrained initial shape;

FIG. 4 is a section IV—IV through the fixing means of FIG. 1;

FIG. 5 is a section V—V through the fixing means of FIG. 1; and

FIG. 6 illustrates front parts of a sleeve with an alternative design and forming part of the fixing means of FIG. 1.

DETAILED DESCRIPTION OF THE INVENTION

Figure 1:
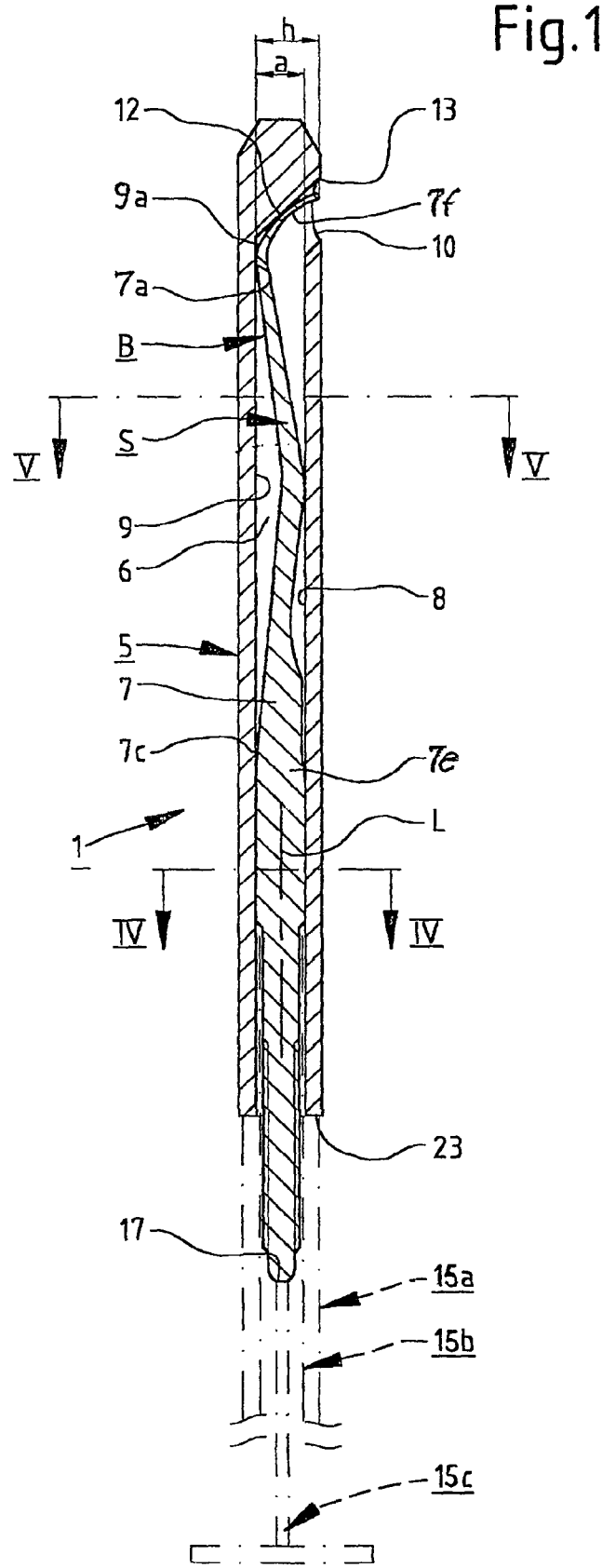
FIG. 1 is a longitudinal section through a fixing means with a device according to the invention.

The fixing means 1 illustrated in the drawings is adapted for fixation of bone fragments at bone fractures. Preferably, the fixing means 1 is a spike for thigh-bone necks, a collum spike, for fixation of bone fragments 2, 3 at fractures 4 of the thighbone neck.

The spike 1 comprises a sleeve 5 with an elongated space 6 which is open at the rear for insertion of a pin 7. The elongated space 6 has a circular or substantially circular cross section.

The sleeve 5 has a first longitudinal wall surface 8 and opposite thereto, a second longitudinal wall surface 9. In the first longitudinal wall surface 8 there is provided a side opening 10 and from a front edge 13 of said side opening 10, a guide surface 12 protrudes in a backwards inclined direction to the second longitudinal wall surface 9.

The pin 7 has a front end portion 7f which preferably is curved. This front end portion 7f is adapted to be guided by the guide surface 12 such that it is forced out of the space 6 through the side opening 10 and into adjacent bone fragment 3.

A front part 7a of the pin 7 close to its front end portion 7f extends in an inclined forward direction towards front parts 9a of the second longitudinal wall surface 9 and is preferably adapted to have contact with said front parts 9a at the guide surface 12 when the pin 7 is in a ready position B (see FIG. 1) from which it can be driven farther into the elongated space 6 in order to force the front end portion 7f out through the side opening 10. In this ready position B, contact members 7b between said front part 7a and an intermediate part 7d of the pin 7 are in contact with the first longitudinal wall surface 8 behind the side opening 10.

The front end portion 7f of the pin 7 preferably has a height h which is greater than the distance a between the first and second longitudinal wall surfaces 8 and 9. Thus, the height h of the front end portion 7f may be about 4,5 mm while the distance a is about 4 mm. The pin 7 is capable of being bent such that the front end portion 7f can be inserted into the elongated space 6 when the pin 7 is moved to the ready position B. When the pin 7 has reached the ready position B, the front end portion 7f can snap into the side opening 10.

When the pin 7 is in the ready position B and/or when it is driven into the elongated space 6 to force its front end portion 7f out through the side opening 10, said front end portion 7f of the pin 7 preferably is in contact with central parts of the guide surface 12 about halfway between the front edge 13 of the side opening 10 and the second longitudinal wall surface 9.

The front end portion 7f of the pin 7 projects preferably into the side opening 10, but not out of the sleeve 5 beyond its outer profiles when said pin 7 is in the ready position B.

The pin 7 is designed relative to the space 6 in the sleeve 5 such that it in the ready position B does not move unintentionally out of said space 6 relative to said sleeve 5.

The pin 7 is adapted to be driven into the sleeve 5 by means of a driving or actuator instrument 15. This instrument may comprise three members schematically illustrated with broken lines in FIG. 1, namely an outer sleeve 15*a* which can be brought to engage the rear edge 23 of the sleeve 5 such that said outer sleeve 15*a* can not turn or rotate relative to the sleeve 5. Said outer sleeve 15*a* can be held in this position by means of an inner sleeve 15*b* having outer threads which permit meshing of said outer sleeve with inner threads in the sleeve 5.

The driving instrument 15 further comprises a driving or actuator unit 15*c* which has outer threads permitting it to be secured to inner threads in the inner sleeve 15*b*. Since thereby the driving unit 15*c* is in contact with the rear edge 17 of the pin 7, it will drive or force the pin 7 into the space 6 in the sleeve 5 and thus, press the front end portion 7*f* of the pin 7 out of the side opening 10, whereby said front end portion 7*f* is deformed.

Driving or actuator instruments of this type are already known from SE 431 053 (U.S. Pat. No. 4,498,468) and therefore not further described here.

The pin 7 is also designed relative to the space 6 of the sleeve 5 such that it can not rotate about its longitudinal axis L if and/or when parts of the driving instrument 15 come in contact therewith when said parts are turned or rotated. This can be achieved by bringing the front end portion 7*f* of the pin 7 to engage the side opening 10 when said pin 7 is in its ready position B.

The pin 7 preferably has elastic properties or at least a front part 7*a* thereof has elastic properties. The pin 7 may e.g. consist of such metallic material that it has elastically resilient properties.

The pin 7 may have an original shape U (see FIG. 3) which is such relative to the shape of the elongated space 6 in the sleeve 5 that said pin 7, during insertion into said elongated space 6 in the sleeve 5, through deformation is brought into such a strained or stretched condition S (see FIG. 1) that it moves or is moved unintentionally relative to the sleeve 5. In order to illustrate the difference there may be between the original shape U of the pin 7 and the shape of the elongated space 6, the latter is shown with broken lines in FIG. 3.

The pin 7 is provided to slide against the front part 9*a* of the second longitudinal wall 9, lying closest to the guide surface 12 when the pin 7 is driven into the elongated space 6. Rear parts 7*e* of the pin 7 are in contact with the second longitudinal wall 9 of the sleeve 5 when the pin 7 is in the ready position B.

In the ready position B, the front end portion 7*f* of the pin 7 is preferably in contact with the guide surface 12 a short distance within the side opening 10, such that when the front end portion 7*f* is forced out through the side opening 10, it assumes a curved shape along its entire or at least the major part of its length.

The pin 7 may, in its original shape U, have a straight or substantially straight rear part 7*e* and the front part 7*a* may be straight or substantially straight and directed obliquely forward/sideways relative to the rear part 7*e* or the pin 7 may e.g. have an S-shape as is shown in FIG. 3.

The front part 7*a* of the pin 7 may have a circular segment-shaped cross section (see FIG. 5) and its rear part 7*e* a circular cross section (see FIG. 4). At the contact part 7*b*, the circular segment-shaped cross section transforms into the circular cross section. Furthermore, the rear part 7*e* of the pin 7 may be in contact with the second longitudinal wall 9 through a contact part 7*c*.

The pin 7 preferably has such a length relative to the length of the elongated space 6 of the sleeve 5 that the rear edge 17 of the pin 7 is situated edge-to-edge with the rear edge 23 of the sleeve or within said rear edge 23 when the pin 7 is fully driven into the sleeve 5. This is advantageous since the pin 7 after finished driving or actuator operation hereby does not project at the rear of the sleeve 5, whereby the risk for tenderness of the patient is reduced.

At the back, the pin 7 is provided with a threaded portion (not shown) which after finished driving or actuator operation is located inside the sleeve 5 and which is adapted for cooperation with a correspondingly threaded portion (not shown) on an extractor unit (not shown) for extraction or removal of the pin 7 from the bone fragment 3.

As is apparent from FIG. 6, front parts 27 of the sleeve 5 may have external threads for securing the sleeve 5 to the bone fragment 3. The outer diameter of the external threads of the front parts 27 may correspond with or substantially correspond with the outer diameter of unthreaded parts of the sleeve 5 behind said front parts 27.

By means of the embodiment defined above and illustrated in the drawings, the pin 7 will thus remain in a ready position B until its front end portion 7*f* has been driven or forced into surrounding bone material 2. Another advantage is that the front end portion 7*f* of the pin 7 will slide against large parts of the guide surface 12 during its displacement, whereby said pin assumes an advantageous curved shape along its entire or almost entire length outside the side opening 10.

The invention is not limited to the embodiment described above and illustrated in the drawings, but may vary within the scope of the subsequent claims regarding the use and design of the various parts and their function. As examples of embodiments and uses not described above, it can be mentioned that the fixing means 1 can be used for bone fractures on other locations than the thigh-bone neck (neck of the femur), the sleeve 5 may be of metal material or another suitable material, the pin 7 may be of another material than metallic material and the sleeve 5 as well as the pin 7 may have other shapes than those illustrated and yet have the same or similar functions as described above.

The invention claimed is:

1. Device which includes a fixing means for fixation of bone fragments at bone fractures, wherein the fixing means (1) preferably is a spike for thigh-bone necks for fixation of bone fragments (2, 3) at fractures (4) of the thigh-bone neck, wherein the fixing means (1) comprises a sleeve (5) which is open at the rear for insertion of a pin (7) into a ready position (B), wherein the sleeve (5) defines an elongated space (6) with two opposite wall surfaces (8, 9), namely a first longitudinal wall surface (8) in which there is provided a side opening (10) and a longitudinal second wall surface (9) from which a guide surface (12) extends in an inclined forward direction to a front edge (13) of the side opening (10), and wherein the guide surface (12) is provided to guide a front, preferably curved end portion (7*f*) of the pin (7) to force its way out through the side opening (10) when said pin (7) is displaced in a forward direction relative to the sleeve (5), characterized in that a portion of the pin (7) closest to the front end portion (7*f*) includes a front part (7*a*) which is directed obliquely forward relative to a rear part (7*e*) of the pin (7) and towards a front parts (9*a*) of the second wall surface (9) close to the guide surface (12) in that the front end portion (7*f*) of the pin (7) engages the side opening (10) when the pin (7) is located in a ready position (B) in the sleeve, an intermediate part (7*d*) of the pin (7) is directed obliquely forward towards the first longitudinal wall surface (8), a contact part (7*b*) between the intermediate part (7*d*) and the front part (7*a*) is in contact with the first longitudinal wall surface (8), and the rear part (7*e*) is in contact with the second longitudinal wall surface (9) when the pin is in the ready position (B), (5) and the pin (7) has a length relative to the length of the elongated space (6) of the sleeve (5) such that a rear edge (17) of the pin (7) is located edge-to-edge with a rear edge (23) of the sleeve (5) or within said rear edge (23) when the pin (7) is fully driven into the sleeve (5), so that the pin (7) after finished driving or actuator operation does not project from the rear of the sleeve (5).

2. Device according to claim 1, characterized in that the front part (7*a*) of the pin (7) is in contact with the front part (9*a*) of the second wall surface (9) when the pin (7) is in the ready position (B).

3. Device according to claim 1, characterized in that the pin (7) is designed such that its front part (7*a*) slides against the front part (9*a*) of the second wall surface (9) when it is driven or forced into the elongated space (6) of the sleeve (5) in order to bring the front end portion (7*f*) of the pin (7) to protrude or force its way out through the side opening (10).

4. Device according to claim 1, characterized in
that the pin (7) has an original shape (U) in which a height (h) of the front end portion (7*f*) is greater than the distance (a) between the first and second longitudinal wall surfaces (8, 9),
wherein the pin (7) is capable of being bent such that the front end portion (7*f*) of the pin (7) can be inserted into the sleeve (5) when the pin (7) is moved to the ready position (B) within the sleeve (5) and
wherein the pin (7) has elastic properties such that the front end portion (7*f*) of the pin (7) snaps into the side opening (10) after having been moved thereto.

5. Device according to claim 1, characterized in that the front end portion (7*f*) of the pin (7) is situated within the outer profile of the sleeve (5) when it engages the side opening (10).

6. Device according to claim 1, characterized in that the front end portion (7*f*) of the pin (7) is in contact with the guide surface (12) when the pin (7) is in the ready position (B).

7. Device according to claim 1, characterized in that the front end portion (7*f*) of the pin (7) is in contact with a central portion of the guide surface (12) about halfway between the front edge (13) of the side opening (10) and the second longitudinal wall surface (9) when the pin (7) is in said ready position (B) and/or when the pin (7) is driven into the elongated space (6) in order to bring the front end portion (7*f*) of the pin (7) to force its way out through the side opening (10).

8. Device according to claim 1, characterized in that the pin (7) has a rear part (7*e*) and an intermediate part (7*d*) each of which has a as well as a front part (7*a*) circular cross section.

9. Device according to claim 1, characterized in that in the ready position (B), the pin (7) is provided such that it does not turn or rotate and/or can turn or rotate about its longitudinal axis (L) relative to the sleeve.

10. Device according to claim 1, characterized in that in the ready position (B), the pin (7) is provided such that it can not rotate about is longitudinal axis (L) relative to the sleeve (5) if it is affected by torsional forces from parts of a driving or actuator instrument (15).

11. Device according to claim 1, characterized in that the pin (7) is mounted in the ready position (B) in a strained or stretched condition.

12. Device according to claim 1, characterized in that the pin (7) has an original shape (U) which deflects from the shape of the elongated space (6) of the sleeve (5) in such a way that the pin (7) is strained or stretched by deformation when it is inserted into a ready position (B) in the elongated space (6).

13. Device according to claim 1, characterized in that the front end portion (7*f*) of the pin (7) is provided such that it is forced out of the side opening (10) as a curved front end portion (7*f*) along is entire or substantially entire length.

14. Device according to claim 1, characterized in that the pin (7) in an original shape (U) has a straight or substantially straight rear part (7*e*) and a straight or substantially straight front part (7*a*) which is directed forward and sideways with respect to the rear part (7*e*).

15. Device according to claim 1, characterized in that the pin (7) or at least a front part (7*a*) of the pin (7) has elastic properties.

16. Device according to claim 1, characterized in that a front part (27) of the sleeve (5) has external threads for securing the front part (27) to adjacent bone fragment (3).

17. Device according to claim 16, characterized in that the outer diameter of the external threads of the front part (27) corresponds or substantially corresponds with the outer diameter of the unthreaded parts of the sleeve (5) behind said front part (27).

\* \* \* \* \*

UNITED STATES PATENT AND TRADEMARK OFFICE
CERTIFICATE OF CORRECTION

| | | |
|---|---|---|
| PATENT NO. | : 7,029,476 B2 | Page 1 of 1 |
| APPLICATION NO. | : 10/343403 | |
| DATED | : April 18, 2006 | |
| INVENTOR(S) | : Henrik Hansson | |

It is certified that error appears in the above-identified patent and that said Letters Patent is hereby corrected as shown below:

Column 4, line 62, after "front" change "parts" to --part--.

Column 4, lines 66, after "sleeve" insert --(5)--.

Column 6, line 7, delete "as well as a front part (7a)".

Column 6, line 45, after "unthreaded" change "parts" to --part.--.

Column 6, line 45, after "behind" change "said" to --the--.

Signed and Sealed this

Third Day of April, 2007

JON W. DUDAS
*Director of the United States Patent and Trademark Office*